219-121 SR
12/23/86 OR 4,631,384

United States Patent [19]

Cornu

[11] Patent Number: 4,631,384

[45] Date of Patent: Dec. 23, 1986

[54] BITUMEN COMBUSTION PROCESS

[75] Inventor: Aymé Cornu, Meylan, France

[73] Assignee: Commissariat a l'Energie Atomique, Paris, France

[21] Appl. No.: 579,813

[22] Filed: Feb. 13, 1984

[30] Foreign Application Priority Data

Feb. 17, 1983 [FR] France ................................ 83 02581

[51] Int. Cl.$^4$ .......................... B23K 9/00; C07C 27/10

[52] U.S. Cl. .......................... 219/121 P; 219/121 PA; 219/121 P; 219/10.41; 208/3

[58] Field of Search ......... 219/121 P, 121 PA, 121 P, 219/10.41, 10.57; 373/22; 110/237; 208/3, 8 R, 11 R

[56] References Cited

U.S. PATENT DOCUMENTS

| | | | |
|---|---|---|---|
| 3,818,845 | 6/1974 | Nakane et al. | 110/8 E |
| 4,141,694 | 2/1979 | Camacho | 219/121 P X |
| 4,338,870 | 7/1982 | Lanier, Jr. | 110/237 X |
| 4,344,839 | 8/1982 | Pachkowski et al. | 219/121 P X |
| 4,398,475 | 8/1983 | McKiel, Jr. | 110/237 X |
| 4,432,942 | 2/1984 | Adachi et al. | 219/121 PA X |
| 4,479,443 | 10/1984 | Faldt et al. | 110/237 X |

FOREIGN PATENT DOCUMENTS

| | | |
|---|---|---|
| 1224861 | 9/1966 | Fed. Rep. of Germany . |
| 2468980 | 5/1981 | France . |

*Primary Examiner*—Clarence L. Albritton
*Assistant Examiner*—M. Lateef
*Attorney, Agent, or Firm*—Pearne, Gordon, Sessions, McCoy, Granger & Tilberry

[57] ABSTRACT

Process for the combustion of bitumen, wherein the bitumen is softened by preheating and is then introduced into a combustion chamber, traversed by oxygen in excess subject to ionization by an intense ultra-high frequency field, so as to raise the surface of the bitumen to a temperature above 1000° C., thereby ensuring its vaporization and rapid combustion in the thus produced oxygen plasma.

4 Claims, 1 Drawing Figure

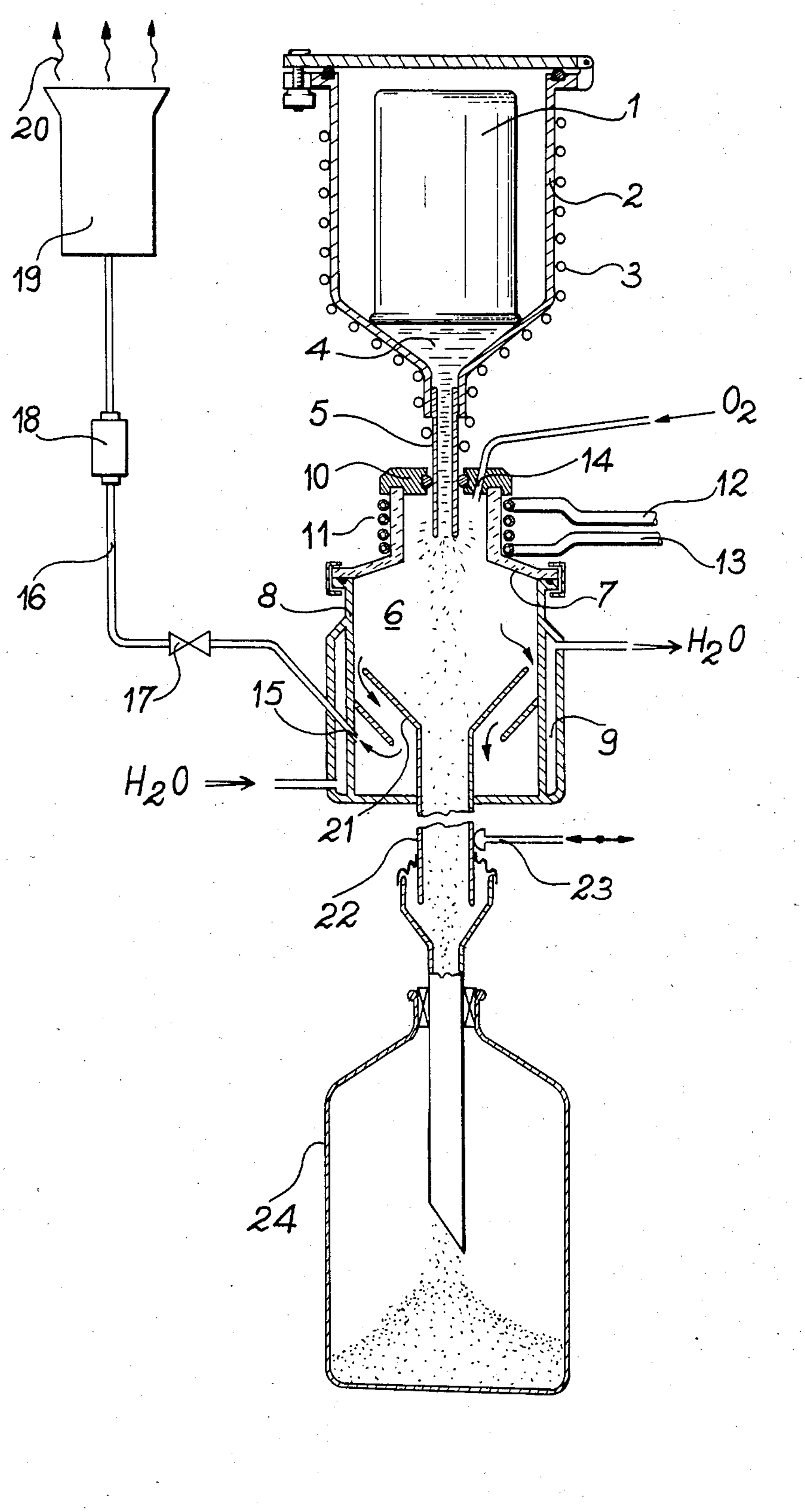
1
2
3
4
5
$O_2$
10
14
12
11
13
8
6
7
$H_2O$
17
15
9
$H_2O$
21
22
23
24
20
19
18
16

BITUMEN COMBUSTION PROCESS

BACKGROUND OF THE INVENTION

The present invention relates to processes for destroying bitumen or pitch by combustion. It more particularly, but non-limitatively, applies to the combustion of bitumen, which has been used in the storage by coating of radioactive waste resulting from the operation of nuclear power stations.

In the industry, there are cases when it is necessary to destroy relatively large bitumen quantities and the first idea is to destroy them by combustion in air or a more or less oxygen-enriched atmosphere. However, it is well known in the art that bitumens, which are essentially constituted by hydrocarbons, only burn with considerable difficulty.

SUMMARY OF THE INVENTION

The object of the present invention is a combustion process, which is particularly effective and easy to perform.

Thus, the present invention relates to a process for the combustion of bitumen, wherein the bitumen is softened by preheating and is then introduced into a combustion chamber, traversed by oxygen in excess subject to ionization by an intense ultra-high frequency field, so as to raise the surface of the bitumen to a temperature above 1000° C. thereby ensuring its vaporization and rapid combustion in the thus produced oxygen plasma.

As a result of the process according to the invention, it is possible to easily burn the bitumen which has previously been softened by preheating, by combining two synergistically acting means, namely the presence of oxygen in excess and the production of a plasma of said gas, which is ionized by a UHF field in order to raise the surface of the bitumen to a temperature above 1000° C. and normally between 1100° and 1300° C.

According to a secondary feature of the present invention, the frequency for the UHF field is preferably between 50 and 100 MHz, whilst the power is 5 to 60 kW.

According to the invention, said UHF heating of the oxygen plasma is an indispensable feature for the satisfactory operation of the bitumen combustion process.

The frequency of the UHF field is adjusted in each individual case, as a function of the composition of the bitumen to be treated. Generally and preferably, a frequency range between 50 and 100 MHz is very suitable and makes it possible to heat the binder rather than the structural materials (such as quartz or the various ceramics).

The useful heating power is usually between 5 and 60 kW and combustion is stopped on dropping the energy below a certain threshold.

The UHF field applied has the effect of bringing about and maintaining both the heating and the vaporization of the pitch in the oxygen atmosphere, the combustion flame generally being very short.

The pitch or bitumen to be destroyed by combustion generally drops in the viscous state by gravity into a combustion chamber with insulating walls, wherein an oxygen pressure of between 1 and 2 bars absolute is maintained.

As each kilogram of pitch produces approximately 10,000 kilocalories as it is being consumed, and as the excitation of the oxygen by UHF gives off a power of several kW, there is a large excess of calories in the combustion chamber which must be removed. Therefore, the combustion chamber is surrounded by an e.g. water-cooled jacket in order to eliminate the radiation heat and which is externally swept by an air flow, which also extracts part of the calories by conduction, the heated water being usable for the preheating of the bitumen.

The present invention also relates to an application of the aforementioned bitumen combustion process to the reprocessing of bitumen containing radioactive waste, in order to separate and recover the latter, which can be used with a view to a subsequent processing or reconditioning.

Thus, it may be necessary to carry out this reprocessing in order to separate the radioactive products and incorporate them into other storage systems, such as glass, concrete or epoxy resins. The process according to the invention makes it possible in this case to convert all the mineral residues and particularly the radioactive waste usually in the form of salts in the bitumen mass into oxides, which are deposited by flocculation in a channel or chute located at the bottom of the combustion chamber, from where they can be transferred and collected in a storage container.

If the precaution is also taken of carrying out the combustion in the presence of an adequate quantity of oxygen (by more particularly regulating the pressure of the gases in the combustion chamber) and by acting on the temperature, i.e. on the power supplied by the generator, all reduction processes are avoided, the pitch burns completely and all the mineral charges are converted into oxides. The combustion gases and the excess oxygen are removed by a duct having an automatic pressure regulating valve protected by a fine filter. The same combustion gases are purified or cleaned by an absolute filter, which removes therefrom all the toxic or radioactive constituents (gases, aerosols, dust, etc.) before discharging them into the atmosphere.

In order to establish that the oxidation of all the products during the combustion in oxygen is complete, a detector of the carbon monoxide contained in these combustion gases is placed at the outlet from the combustion chamber and makes it possible to warn the operator. If such a gas is detected, it is then merely necessary to increase the oxygen pressure and/or temperature in order to increase the oxygenation level, i.e. the combustion level of the pitch and waste or the various constituents thereof. Under these conditions, the only combustion gases passing into the atmosphere after passing through the absolute filter are oxygen, carbon dioxide gas, water and sulphur dioxide, as a function of the sulphur content of the bitumen consumed. In certain cases, it may prove necessary to purify the $SO_3$ ions which may have been produced and which may be contained in the combustion gases.

The performance of the process according to the invention has a certain number of advantages and these are summarized hereinafter.

This process ensures a complete combustion of the bitumen and produces the minimum of combustion gases to be discharged into the atmosphere. Thus, combustion in pure, very high temperature oxygen, makes it possible, without the use of a complicated pulverization system, to obtain a total combustion without any production of pulverulent carbon with a high adsorbing power.

Moreover, the process only uses the oxygen quantity necessary for combustion, but with a slight excess to obviate risks of inadequate oxidation, but without nitrogen, which in the case where air was used, would constitute an important reaction retardant and would also produce very noxious nitrogen oxides.

The volume of the installation is reduced to the strict minimum and the combustion chamber made from refractory material, such as quartz or alumina, is completely sealed, with the exception of the oxygen circulation, which facilitates the confinement of the radioactive products which are the residue of the combustion process. These products resulting from the initial radioactive charge of the bitumen and the normal bitumen ash are obtained in the form of a dry powder with a maximum oxidation level, i,e. in a state permitting their easy use for a subsequent vitrification treatment or for insertion into concrete or an epoxy resin, if this is found to be necessary.

DESCRIPTION OF THE DRAWING AND PREFERRED EMBODIMENTS

The invention is described in greater detail hereinafter relative to non-limitative embodiments and with reference to the single drawing which, in the form of a diagrammatic section along the axis, shows a possible installation for performing the present process.

It is possible to see a pitch drum 1 turned upside down into a funnel-shaped container 2, equipped with an electrical resistor or a heating liquid circulation 3 making it possible to bring about the preheating and softening of the pitch flowing out from the lower part of container 2.

An alumina pipe 5 passes this molten pitch into the combustion chamber 6, whose upper part 7 is made from quartz and whose lower part 8 is made from stainless steel with a lateral jacket 9 traversed by a cooling water flow. In the upper part of chamber 6, there is an alumina joint 10 ensuring the sealing with the alumina pipe 5 and around the quartz cylindrical part of conduction chamber 6 there are a certain number of coils 11 supplied with very high frequency electric current by conductors 12 and 13. Chamber 6 has an inlet 14 for admitting pressurized oxygen and an outlet 15 for the discharge of the reaction gases and excess oxygen. On discharge duct 16 there is also an automatic flow regulating valve 17 making it possible to control the quantity and pressure of the oxygen traversing combustion chamber 6, a detector 18 of the carbon monoxide which may be present in the exhaust gases and an absolute filter 19, at the outlet of which the purified combustion gases are discharged into the atmosphere in accordance with the direction indicated by arrows 20.

In the axis of chamber 6, there is also a funnel-shaped collector 21, which collects the ash from the combustion of bitumen 4 in chamber 6 and conveys said ash by gravity into a channel or chute 22, which is subject to the vibrations of a percussion hammer 23, from where it passes into a container 24 for collecting the radioactive ash and located in the lower part of the installation.

In the aforementioned installation, the pitch 4 is preheated in container 2 by means of a heating means 3 to a temperature of approximately 100° to 150° C., as a function of its softening point. A grid calibrated to ¼ of the diameter of the discharge tube and not shown in the drawing, can be used for holding back the largest particles. On leaving the ceramic pipe 5, the pitch is rapidly superheated with the aid of the intense UHF field produced by coils 11, the frequency of said field being approximately 100 MHz in a particular embodiment. The electric power used is approximately 5 to 60 kW in order to raise the pitch surface to a temperature which, in the present embodiment, is between 1100° and 1300° C. It is then vaporized and rapidly burned in the presence of oxygen injected in vortex-like manner around the pipe, all the mineral residues being converted into oxides by means of the power given off by induction in the thus produced oxygen plasma and at the pressure of said oxygen, which is e.g. chosen as 1 to 2 bars absolute.

In order to complete the cooling of the combustion chamber 6 where a large number of calories is given off, it is possible to add to the water jacket 9 an application of a cold air flow to the walls by means of any known, not shown device.

As stated hereinbefore, the flow rate and pressureof the oxygen gas entering container 6 at 14 are chosen in such a way that the combustion takes place in the presence of an excess of said gas so as to prevent any incomplete combustion, which would then be detected in the form of carbon monoxide at detector 18. In this hypothesis, it is obviously sufficient to act on the oxygen flow rate and pressure, as well as on the UHF power transmitted to chamber 6 to ensure that the pitch and all the products contained therein undergo maximum oxidation. At the outlet 20 from absolute filter 19 only appear $O_2$, $CO_2$, $H_2O$ and $SO_2$, which are completely free from any trace of radioactivity, or corrosive aerosols or dust.

Thus, as the combustion parameters are completely known, it is possible in an improved version of the device shown in the drawing, to automatically regulate the operation, particularly on the basis of an automatic regulating valve 17.

Obviously, constructional variants are possible without passing beyond the scope of the present invention. Thus, the oxygen can be supplied to chamber 6, e.g. with the aid of a pipe coaxial to the alumina pipe 5, or the walls of chamber 6 could be made from quartz or alumina instead of, as in the present embodiment, partly from quartz and partly from stainless steel. However, it is obvious that the transmission of the UHF energy supplied by coils 11 can only take place in chamber 6 through a wall which does not conduct electricity, such as a quartz or alumina wall.

What is claimed is:

1. A process for the combustion of bitumen, wherein the bitumen is softened by preheating and is then introduced into a combustion chamber, traversed by an amount of oxygen and subjected to ionization by an intense ultra-high frequency field, said amount of oxygen being in excess of the quantity of oxygen necessary for combustion of the bitumen, so as to raise the surface of the bitumen to a temperature above 1000° C., thereby ensuring its vaporization and rapid combustion in the thus produced oxygen plasma.

2. A bitumen combustion process according to claim 1, wherein a frequency preferably between 50 and 100 MHz and a power between 5 and 60 kW are preferably chosen for the UHF electric field.

3. A process for separating and recovering radioactive waste from bitumen comprising the steps of preheating the bitumen containing the radioactive waste and then introducing it into a combustion chamber traversed by an amount of oxygen and subjected to ionization by an intense ultra-high frequency field, said amount of oxygen being in excess of the quantity of oxygen necessary for combustion of the bitumen, so as to raise the surface of the bitumen containing the radioactive waste to a temperature above 1000° C., thereby ensuring vaporization and rapid combustion of bitumen in the thus produced oxygen plasma, the remaining radioactive waste being thus separated from the bitumen.

4. The process according to claim 3, wherein a frequency preferably between 50 and 100 MHz and a power between 5 and 60 kW are preferably chosen for the UHF electric field.

* * * * *